United States Patent
Lemann

(10) Patent No.: US 6,403,107 B1
(45) Date of Patent: Jun. 11, 2002

(54) COSMETIC COMPOSITION CONTAINING A HYDROPHILIC CONTINUOUS PHASE CONTAINING BISMUTH VANADATE

(75) Inventor: Patricia Lemann, Creteil (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/437,112

(22) Filed: Nov. 10, 1999

(30) Foreign Application Priority Data

Nov. 10, 1998 (FR) .............................. 98 14159

(51) Int. Cl.$^7$ ............................ A61K 6/00; A61K 7/00; A61K 7/04; A61K 7/025; A61K 7/035
(52) U.S. Cl. ........................... 424/401; 424/61; 424/64; 424/69; 424/70.1; 424/70.7
(58) Field of Search ................ 424/401, 70.1, 424/70.7, 61, 69, 64; 514/937, 938; 106/415

(56) References Cited

U.S. PATENT DOCUMENTS 6,203,807 B1 * 3/2001 Lemann ...................... 424/401

FOREIGN PATENT DOCUMENTS

EP          0 632 110 A1      1/1995

* cited by examiner

*Primary Examiner*—Thurman K. Page
*Assistant Examiner*—S. Howard
(74) *Attorney, Agent, or Firm*—Oblon, Spivak, McClelland, Maier & Neustadt, P.C.

(57) ABSTRACT

A colored composition for topical application, which comprises, a hydrophilic continuous phase comprising bismuth vanadate as a coloring agent.

20 Claims, No Drawings

COSMETIC COMPOSITION CONTAINING A HYDROPHILIC CONTINUOUS PHASE CONTAINING BISMUTH VANADATE

BACKGROUND OF THE INVENTION

1. Field of the Invention

The present invention relates to cosmetic compositions containing a yellow pigment of intense, saturated color which does not generate free radicals. More particularly, the invention relates to make-up compositions for the skin both of the human face and body, the lips and superficial body growths such as the nails, the eyelashes, the eyebrows and the hair.

2. Description of the Background

Make-up compositions such as foundations, face powders, eyeshadows, lipsticks, concealers, blushers, mascaras, eyeliners, lip pencils, eye pencils and nail varnishes and make-up products for the body consist of a suitable vehicle and coloring agents of various natures, intended to impart to these compositions a certain color, before and/or after applying them to the skin, the lips and/or the superficial body growths.

These coloring agents can be lakes, inorganic or organic pigments and/or pearlescent pigments, and alternatively dyes. In the range of yellow pigments, cosmeticians have available pigments of inorganic origin such as yellow iron oxides and pigments of organic origin. Inorganic pigments, and in particular inorganic oxides, have the advantage of being relatively stable, but have the drawback of imparting rather dull, pale colors to the material being colored. Organic lakes have the advantage of imparting lively colors to the compositions, but are mostly unstable with respect to light, temperature or pH. Some of these lacquers also have the drawback of leaving unsightly marks on the skin or the nails after application, by running of the dye. As for pearlescent pigments, they allow varied, but never intense, colors to be obtained, with iridescent effects, but these are usually fairly weak.

Moreover, certain coloring agents have the drawback of generating free radicals in make-up formulations, which modify the color of the applied make-up and the stability of the compositions, and then on the skin after application, which promotes ageing of the skin such as the appearance of wrinkles, fine lines and yellowing of the skin. In particular, yellow iron oxides often promote the oxidation of polyunsaturated oils such as plant oils, which limits the range of compositions. Coloring agents which exhibit this drawback include, in particular, brown-yellow iron oxide mixtures sold under the trade name "Sicovit Yellow 10 E 172" by BASF, for example, pigments of organic origin and the aluminium lake of tartrazine on alumina (20/80) (CI: 19140, CI:77002) sold under the trade name FD & C Yellow 5 by Warner Jenkinson.

At the present time, in order to overcome this problem, antioxidants such as ethoxyquine, for example, are used. Unfortunately, it is often difficult to find an antioxidant which is 100% effective given the multitude of ingredients present in make-up compositions. Furthermore, the antioxidants themselves often generate degradation products including the oxidation of the antioxidant which can cause interference.

SUMMARY OF THE INVENTION

Accordingly, one object of the present invention is to provide, for use in a cosmetic composition, a specific yellow pigment of intense, saturated color, which is stable and which has the advantage of generating far fewer free radicals than the conventional pigments employed in particular for imparting a yellow color to cosmetic compositions.

Briefly, this object and other objects of the present invention as hereinafter will become more readily apparent can be attained by a colored composition for topical application, which comprises a hydrophilic continuous phase comprising bismuth vanadate as a coloring agent.

DETAILED DESCRIPTION OF THE PREFERRED EMBODIMENTS

Surprisingly, it has now been found that bismuth vanadate ($BiVO_4$) limits the production of free radicals, since it has the property of generating very few free radicals, and thus permits a limitation on the amounts of antioxidants which are used in compositions. In addition, the pigment of the invention makes it possible to achieve an intense coloration of a composition containing the colorant and, in particular, a very bright, intense lemon-yellow color of very great color purity, which does not run on keratin substances and is stable with respect to light, pH and temperature. In addition, the pigment broadens the color range which can be achieved in the cosmetics field and participates in the creation of vivid greens by mixing bright oranges with blues. Furthermore, the pigment reduces the amount of pigment which needs to be incorporated in a cosmetic composition in comparison to the amounts of conventional pigment needed in conventional prior art cosmetic formulations, thus making it possible to preserve the sheen of the composition, as well as that of the film deposited, which is highly desired for nail varnishes and make-up products for the lips.

More specifically, an aspect of the present invention is a colored composition for topical application, which contains a hydrophilic continuous phase and more especially a cosmetic make-up composition containing a hydrophilic continuous phase containing bismuth vanadate ($BiVO_4$) as coloring agent and more specifically, as a pigment. This pigment can be in a pure form or deposited on substrate. In particular, this pigment in pure form is sold by BASF under the name Sicopal Gelb L1100.

The manufacture of this pigment is, in particular, described in EP 0 551 637 and EP 0 632 110 of BASF. The pigment has a particle size of about 0.3 μm.

Bismuth vanadate can crystallize in various forms and in so doing expresses different yellow tones. Thus, the monoclinic lattice form, fergusonite, is a bright yellow having a density of 6.959; the tetragonal lattice form, zircon, is pale yellow having a density of 6.127; the tetragonal lattice form, scheelite, is bright yellow having a density of 6.929 and the orthorhombic lattice form, pulcherite, is pale yellow.

The property of bismuth vanadate of not generating free radicals can be demonstrated by the ethylene test described in the article "Ethylene formation from methionine as a method to evaluate oxygen free radical scavenging and metal inactivation by cosmetics" by J.-B. Galey, F. Millecamps and Q.-L. Nguyen, International Journal of Cosmetic Science, 13, 65–78, 1991.

An object of the invention is to compare the behavior of the inorganic pigment of the invention with the behavior of conventional pigments in a photo-oxidation test using iron as free-radical generator.

In the ethylene test measurement procedure, the $FeCl_3$ used to activate the production of free radicals was replaced with each of the pigments to be tested. The results are shown in the table below.

| DYE | ETHYLENE PRODUCED (peak area) | | |
|---|---|---|---|
| Concentration | 0.01% | 0.1% | 0.2% |
| Yellow iron oxide (CI:77492) | 13,500 | 30,000 | 50,000 |
| Bismuth vanadate | 5,000 | 5,500 | 5,000 |

The control of $FeCl_3$ at 0.005% is on average 9000 (arbitrary unit—relative measurement).

The greater the amount of ethylene, the greater the production of free radicals.

Yellow iron oxide (CI:77492) is not inert. At low dose, it activates up to a certain concentration at which the protective effect of the pigment comes into play, whereas for bismuth vanadate, the degree of ethylene produced is very low and does not change as a function of the concentration. This pigment may thus be used advantageously in make-up compositions and colored antisun compositions intended in particular for protecting the skin and/or mucous membranes such as the lips, without generating free radicals and thus limiting the degradation of the skin and/or the mucous membranes.

Compared with the yellow iron oxides commonly used in cosmetics, the pigment of the invention also has the advantage of having a higher saturation of color, i.e., more vivid and of a more intense color, which makes it possible, in particular, to use in smaller amount of pigment, for an equivalent color yield.

The calorimetric parameters of bismuth vanadate sold by BASF under the trade name Sicopal Gelb L1100 relative to those of yellow iron oxide (CI:77492) are given below.

| Parameter | Yellow iron oxide | Bismuth vanadate |
|---|---|---|
| L | 69.9 | 92.8 |
| a | 6.85 | −12.92 |
| b | 50.35 | 84.64 |
| c | 50.6 | 85.27 |

The higher the value of c, the more saturated the color. Bismuth vanadate has a more vivid, more intense color than iron oxide, thus allowing a cosmetic composition to be strongly colored with a small amount of pigment. Thus, the rheological problems (difficulty of application, non-uniform make-up effect) associated with an excessively large amount of pigment in the compositions of the prior art are largely attenuated.

Compared with an organic lake, bismuth vanadate gives better coverage for an equal amount of pigment.

The pigment of the invention can be incorporated into a cosmetic composition containing a hydrophilic continuous phase, in particular a make-up composition, in an amount which can readily be determined by one of skill in the art on the basis of the skilled artisan's general knowledge. The amount of pigment ranges in particular from 0.01 to 50% by weight relative to the weight of the composition, preferably an amount ranging from 0.5 to 25% by weight. Even at high concentration, the pigment of the invention does not destructure the composition.

The composition of the invention can be in the form of a product to be applied to the lips, the eyes, the skin and/or the superficial body growths of human beings. It, therefore, contains a cosmetically acceptable medium, i.e. a medium which is compatible with all keratin substances, such as the skin both of the human body and face, the nails, the hair, the eyelashes and the eyebrows.

In the present invention, the medium contains a hydrophilic continuous phase, i.e. a mixture of one or more hydrophilic substances which are at least partly miscible with or soluble in water, which can be liquid, pasty or solid at room temperature (25° C. in general). In particular, the medium comprises or can be in the form of a suspension, dispersion or solution in water or an aqueous-alcoholic medium, which is optionally thickened, or even gelled; an oil-in-water (O/W) emulsion or a multiple (W/O/W) emulsion, in the form of a cream, a paste or even a solid; an aqueous or aqueous-alcoholic gel or a hydrophilic foam; an emulsified gel; a dispersion of vesicles, in particular of ionic or nonionic lipids; a two-phase or multiphase lotion; a spray. A person skilled in the art can select the appropriate pharmaceutical form, as well as the method for preparing it, on the basis of knowledge which the skilled artisan has, given, on the one hand, the nature of the constituents used, in particular their solubility in the support, and, on the other hand, the application envisaged for the composition.

The composition thus comprises a hydrophilic continuous phase which may contain water or a mixture of water and at least one hydrophilic organic solvent such as an alcohol and in particular a linear or branched lower monoalcohol containing from 2 to 5 carbon atoms such as ethanol or propanol, a polyol such as glycerol, diglycerol, propylene glycol, sorbitol, panthenol, pentylene glycol or polyethylene glycol. This continuous phase can represent from 0.5 to 99.99% of the total weight of the composition. In addition, it can contain hydrophilic $C_2$–$C_4$-aldehydes and $C_2$ ethers.

When the composition of the invention is in the form of an emulsion, it can also optionally comprise a surfactant, preferably in an amount of from 0 to 30% and in particular from 0.01 to 30% by weight relative to the total weight of the composition.

Depending on the application envisaged, the composition can also comprise a film-forming polymer such as a polyurethane, a polyacrylic, a polyurethane and a polyacrylic hybrid, a polyester, nitrocellulose, a hydrocarbon-based resin and/or a silicone resin. This is especially the case when it is desired to prepare a composition such as a water-based nail varnish, a mascara, an eyeliner or a hair composition such as a lacquer. The polymers can be dissolved or dispersed in the cosmetically acceptable medium and optionally combined with a coalescing agent and/or plasticizer.

The composition of the invention may also comprise a fatty phase, in particular a fatty phase consisting of fatty substances which are liquid at room temperature (25° C. in general) and/or fatty substances which are solid at room temperature, such as waxes, pasty fatty substances, gums and mixtures thereof. This fatty phase may also contain lipophilic organic solvents.

Suitable fatty substances which are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or alternatively sunflower oil, corn oil, soybean oil, grapeseed oil, sesame oil, apricot oil, macadamia oil, castor oil, avocado oil, caprylic/capric acid triglycerides, jojoba oil, karite butter; linear or branched hydrocarbons of mineral or synthetic origin such as liquid paraffins and derivatives thereof, petroleum jelly, polydecenes, hydrogenated polyisobutene such as parleam; synthetic esters and ethers, in particular of fatty acids such as, for example, purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates and decanoates of fatty alcohols; polyol esters such as propylene glycol dioctanoate, neopentyl glycol diheptanoate, diethylene glycol diisononanoate; and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) which are liquid or pasty at room temperature such as cyclomethicones and dimethicones, optionally comprising a phenyl group, for instance phenyl trimethicones, phenyltrimethylsiloxydiphenylsiloxanes, diphenylmethyldimethyltrisiloxanes, diphenyl dimethicones, phenyl dimethicones, polymethylphenyl siloxanes; mixtures thereof.

These oils are usually present in an amount of 0 to 90%, preferably from 0 to 85% by weight relative to the total weight of the lipophilic phase.

The lipophilic phase of the composition of the invention may also comprise one or more cosmetically acceptable organic solvents, with the term acceptable relating to the properties of tolerance, toxicology and feel. These solvents are present in an amount of 0 to 60%, preferably 0 to 30% of the total weight of the composition and can be selected from the group consisting of lipophilic organic solvents, amphiphilic organic solvents and mixtures thereof. Suitable solvents which can be used in the composition of the invention include acetic acid esters such as methyl, ethyl, butyl, amyl or 2-methoxyethyl acetate; ketones such as methyl ethyl ketone, methyl isobutyl ketone, isopropyl acetate; hydrocarbons such as toluene, xylene, p-cylene, hexane or heptane; aldehydes containing from 5 to 10 carbon atoms; ethers containing at least 3 carbon atoms; and mixtures thereof.

The composition of the invention may further comprise any ingredient conventionally used in the fields under consideration, and more especially in cosmetics and dermatology. These ingredients include, in particular, preserving agents, aqueousphase thickeners (polysaccharide biopolymers, synthetic polymers) and fatty-phase thickeners, fragrances, hydrophilic and lipophilic active agents and mixtures thereof. The amounts of these various ingredients are those conventionally used in the fields under consideration, and, for example, from 0.01 to 20% of the total weight of the composition. The nature of these ingredients and their amounts must be compatible with the production of stable, thickened, glossy compositions of the invention.

The composition of the invention may also comprise an additional particulate phase which can be present in an amount of 0 to 30% of the total weight of the composition, preferably from 0.05 to 20%, and which can comprise pigments and/or pearlescent agents and/or fillers used in cosmetic compositions.

The term "pigments" should be understood as meaning white or colored, inorganic or organic particles which are insoluble in the liquid hydrophilic phase and which are intended to color and/or opacity the composition. The term "fillers" should be understood as meaning colorless or white, inorganic or synthetic, lamellar or non-lamellar particles. The term "pearlescent agents" should be understood as meaning iridescent particles, in particular produced by certain molluscs in their shell or synthesized pearlescent particles. These fillers and pearlescent agents serve in particular to modify the texture of the composition.

Pigments other than bismuth vanadate can be present in the composition in an amount of 0 to 25% of the weight of the final composition, and preferably in an amount of 2 to 15%. Suitable inorganic pigments include titanium oxide, zirconium oxide and cerium oxide, as well as zinc oxide, iron oxide, chromium oxide and ferric blue. Suitable organic pigments which can be used include carbon black and barium, strontium, calcium or aluminium lakes or alternatively the diketopyrrolopyrroles (DPP) described in EP 0 542 669, EP 0 787 730, EP 0 787 731 and WO 96/08537.

The pearlescent agents can be present in the composition in an amount of 0 to 20% of the total weight of the composition, preferably an amount ranging from 1 to 15%. Suitable pearlescent agents include mica coated with titanium oxide, with iron oxide, with natural pigment or with bismuth oxychloride, such as colored titanium mica.

The filler component is normally present in an amount of 0 to 30% of the total weight of the composition, preferably 0.5 to 15%. Suitable fillers include talc, zinc stearate, mica, kaolin, Nylon (in particular orgasol) powder, polyethylene powder, Teflon, starch, boron nitride, copolymer microspheres such as Expancel (Nobel Industrie), Polytrap (Dow Coming) and silicone resin microbeads (Tospearl from Toshiba, for example).

The composition of the invention advantageously comprises a solid or pasty fatty phase containing one or more gums and/or one or more waxes. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C.

Suitable waxes include beeswax, camauba wax or candelilla wax, paraffin, microcrystalline waxes, ceresin or ozokerite; synthetic waxes such as polyethylene waxes and Fischer-Tropsch waxes, silicone waxes such as alkyl- or alkoxydimethicones containing from 16 to 45 carbon atoms.

The gums are generally high molecular weight PDMSs or cellulose gums or polysaccharides and the pasty substances are generally hydrocarbon-based compounds such as lanolins and derivatives thereof or alternatively PDMSS.

The nature and amount of the solid substances depend on the desired mechanical properties and textures. As a guide, the composition can contain from 0 to 50% by weight of waxes relative to the total weight of the composition, preferably from 1 to 30%.

This composition can have the appearance of a cream, salve, fluid lotion, soft paste with a dynamic viscosity at 25° C. ranging from 1 to 40 Pa.s, ointment or a solid which is poured or cast and in particular as a stick or a dish.

The composition of the invention can be used advantageously for making-up the skin and/or the lips and/or the superficial body growths depending on the nature of the constituents used. In particular, this composition can be a tube of lipstick or a lip lacquer, a lip gloss which can be used just as it is or for application to a film of lipstick in particular to increase its gloss and/or its color (known as a topcoat). It can also be a solid foundation, a concealer product or a product for the contours of the eyes, an eyeliner, a mascara, an eyeshadow, a blusher or a nail varnish. These compositions can also contain cosmetic or dermatological active agents, in particular in order to give the composition a care or treating appearance. Thus, the composition can contain vitamins and other lipophilic active agents such as lanolin or a UVA screening agent or a hydrophilic active agent such as a hydrating agent such as glycerol.

An aspect of the invention is the use of the above composition as a cosmetic to care for and/or make-up and/or protect the skin and/or the lips and/or the superficial body growths of human beings, as well as the use of this composition for the preparation of an ointment intended to treat and/or protect the skin and/or the lips and/or the superficial body growths. Another aspect of the invention is a cosmetic treatment process for the skin and/or the lips and/or the superficial body growths, which consists in applying the composition defined above to the skin and/or the lips and/or the superficial body growths.

In particular, a preferred aspect of the invention is a lip product, a foundation or a nail varnish.

The composition of the invention can be obtained by a process of preparation conventionally used in cosmetics or dermatology.

A further aspect of the invention is the use, in a colored cosmetic composition or for the manufacture of a colored dermatological composition, of a coloring agent as described above, in order to protect the skin and/or the lips and/or the superficial body growths against the harmful effects of free radicals and/or to combat the signs of ageing, in particular photo-induced ageing, of the skin. These signs of ageing are, in particular, wrinkles, fine lines and flaccid and/or yellowed skin.

Still a further aspect of the invention is a process for the cosmetic protection of the skin and/or the lips and/or the superficial body growths against the harmful effects of free radicals and/or for combating the signs of photo-induced ageing of the skin, which consists in applying the composition as defined above to the skin and/or the lips and/or the superficial body growths, Having generally described this invention, a further understanding can be obtained by reference to certain specific examples which are provided herein for purposes of illustration only and are not intended to be limiting unless otherwise specified.

The percentages given in the Examples are percentages by weight.

EXAMPLE 1

O/W Type Foundation

| Phase A: | |
|---|---|
| Stearic acid | 2.0% |
| Glyceryl stearate | 3.0% |
| Glyceryl isostearate | 2.0% |
| Mineral oil | 8.0% |
| Pigments | |
| Red iron oxide | 0.9% |
| Black iron oxide | 0.3% |
| Titanium dioxide | 4.4% |
| Bismuth vanadate | 0.7% |
| Preserving agent | 0.2% |
| Dimethicone (5 cst) to be verified | 4.0% |

-continued

| Phase B: | |
|---|---|
| Triethanolamine | 1.0% |
| Phase C: | |
| Preserving agent | 0.2% |
| Magnesium aluminum silicate as a gel containing 5% active material | 20.0% |
| Cellulose gum | 3.5% |
| Sodium lauroyl sarcosinate | 3.5% |
| Glycerol | 2.0% |
| Water | qs 100% |
| Phase D: | |
| Preserving agent | 0.3% |
| Water | 2.0% |

Procedure

Phases A and C are prepared separately. They are heated to 80° C. and are then homogenized using a homogenizer sold under the name Moritz. Phase B is introduced into phase A and this mixture is then poured into phase C with stirring. Phase D is then added and stirring is continued until completely cold.

A beige-colored foundation which has high covering power, is stable to light and leaves no scratches (or marks) after removal of the make-up is obtained.

EXAMPLE 2

Lip Lacquer Composition

| Aqueous dispersion of acrylic polymer/styrene (Neocryl A-1052 from Zeneca) | 20.0% active material |
|---|---|
| Acetyl tributyl citrate | 2.5% |
| Bismuth vanadate | 1.5% |
| Flaming Red (CI 12085) | 1.5% |
| Glycerol | 1.25% |
| Water | qs 100% |

Procedure

The acetyl tributyl citrate, the pigments and the aqueous phase (glycerol+water) are added, at room temperature, to the polymer dispersion, followed by homogenization.

A stable, orange-colored lip lacquer which gives good coverage is obtained.

The disclosure of French priority Application Number 9814159 filed Nov. 10, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A colored composition for topical application, which comprises:
    a hydrophilic continuous phase comprising bismuth vanadate as a coloring agent.

2. The composition according to claim 1, wherein the coloring agent is present in an amount of 0.01 to 50% by weight relative to the weight of the composition.

3. The composition according to claim 2, wherein the coloring agent is present in an amount of 0.5 to 25% by weight.

4. The composition according to claim 1, wherein the bismuth vanadate coloring agent is the monoclinic lattice form, fergusonite having a bright yellow color with a density of 6.959, the tetragonal lattice form, zircon, having a pale yellow color with a density of 6.127, the tetragonal lattice form, scheelite, having a bright yellow with a density of 6.929 and the orthorhombic lattice form, pulcherite, having a pale yellow color.

5. The composition according to claim 1, wherein the hydrophilic continuous phase contains water or a mixture of water and hydrophilic solvents.

6. The composition according to claim 1, wherein the hydrophilic continuous phase comprises a monoalcohol, a polyol, a hydrophilic $C_2$–$C_4$-aldehyde or a $C_2$ ether.

7. The composition according to claim 6, wherein the hydrophilic solvent is the monoalcohol, ethanol or propanol and said polyol is glycerol, diglycerol, propylene glycol, sorbitol, panthenol, pentylene glycol or polyethylene glycol.

8. The composition according to claim 6, wherein the hydrophilic continuous phase is 0.5 to 99.99% of the total weight of the composition.

9. The composition according to claim 1, which is in the form of an emulsion containing a surfactant in an amount of 0 to 30% by weight based on the total weight of the composition.

10. The composition according to claim 1, which further comprises a film-forming polymer selected from the group consisting of a polyurethane, a polyacrylic, a polyurethane and a polyacrylic hybrid, a polyester, nitrocellulose, a hydrocarbon-based resin, a silicone resin and combinations thereof.

11. The composition according to claim 1, which further comprises at least one fatty phase selected from the group consisting of oils, waxes, gums, pasty fatty substances, lipophilic organic solvents and mixtures thereof.

12. The composition according to claim 11, wherein said oil is perhydrosqualene; a hydrocarbon-based liquid triglycerides plant oil selected from the group consisting of heptanoic or octanoic acid triglycerides, sunflower oil, corn oil, soybean oil, grapeseed oil, sesame oil, apricot oil, macadamia oil, castor oil, avocado oil, caprylic/capric acid triglycerides, jojoba oil and karite butter; a linear or branched hydrocarbon of mineral or synthetic origin selected from the group consisting of liquid paraffins, derivatives thereof, petroleum jelly, polydecenes and hydrogenated polyisobutene; a synthetic ester or ether of a fatty acid selected from the group consisting of purcellin oil, isopropyl myristate, 2-ethylhexyl palmitate, 2-octyldodecyl stearate, 2-octyldodecyl erucate and isostearyl isostearate; a hydroxylated ester selected from the group consisting of isostearyl lactate, octyl hydroxystearate, octyldodecyl hydroxystearate, diisostearyl malate, triisocetyl citrate; heptanoates, octanoates and decanoates of fatty alcohols; polyol esters selected from the group consisting of propylene glycol dioctanoate, neopentyl glycol diheptanoate, diethylene glycol diisononanoate; and pentaerythritol esters; $C_2$–$C_{26}$-fatty alcohols selected from the group consisting of octyldodecanol, 2-butyloctanol, 2-hexyldecanol, 2-undecylpentadecanol, oleyl alcohol; partially hydrocarbon-based fluoro oils and/or fluorosilicone oils; and a volatile or non-volatile, linear or cyclic polymethylsiloxanes which is liquid or pasty at room temperature selected from the group consisting of cyclomethicones and dimethicones, a phenyl group substituted polymethylsiloxane selected from the group consisting of phenyl trimethicones, phenyltrimethylsiloxydiphenylsiloxanes, diphenylmethyldimethyltrisiloxanes, diphenyl dimethicones, phenyl dimethicones, polymethylphenyl siloxanes and mixtures thereof.

13. The composition according to claim 11, wherein the oil is present in an amount of 0 to 90% relative to the total weight of the lipophilic phase.

14. The composition according to claim 13, which further comprises an additional particulate phase which is present in an amount of 0 to 30% of the total weight of the composition.

15. The composition according to claim 1, which is in the form of a make-up product for the skin, the lips and/or the superficial body growths of a human being.

16. The composition according to claim 1, which is in the form of a nail varnish, mascara, eyeliner, hair composition, lip product, lip gloss, foundation, concealer product, face powder, eyeshadow or body make-up.

17. The composition according to claim 1, which is in the form of an oil in water emulsion or a dispersion of polymer in an aqueous or aqueous-alcoholic medium, or in the form of a gel.

18. A method of cosmetically treating the skin, comprising:
applying the composition according to claim 1 to the skin, the lips and/or superficial body growths.

19. A method of treating or protecting the skin, comprising:
applying the composition according to claim 1 in the form of an ointment to the skin, the lips and/or superficial body growths.

20. A method for the cosmetic protection of the skin, the lips and/or superficial body growths, comprising:
applying the composition according to claim 1 to the skin, the lips and/or superficial body growths, thereby protecting these body components against the harmful effects of free radicals and/or combating the signs of photo-induced ageing of the skin.

* * * * *

UNITED STATES PATENT AND TRADEMARK OFFICE
CERTIFICATE OF CORRECTION

PATENT NO. : 6,403,107 B1
DATED : June 11, 2002
INVENTOR(S) : Patricia Lemann

It is certified that error appears in the above-identified patent and that said Letters Patent is hereby corrected as shown below:

Column 10,
Line 4, "$C_2$-$C_{26}$" should read -- $C_{12}$-$C_{26}$ --.

Signed and Sealed this

Nineteenth Day of November, 2002

Attest:

Attesting Officer

JAMES E. ROGAN
Director of the United States Patent and Trademark Office